(12) United States Patent
Kermani et al.

(10) Patent No.: US 6,797,150 B2
(45) Date of Patent: Sep. 28, 2004

(54) DETERMINATION OF SAMPLE VOLUME ADEQUACY IN BIOSENSOR DEVICES

(75) Inventors: Mahyar Z. Kermani, Pleasanton, CA (US); Maria Teodorczyk, San Jose, CA (US); Sherry X. Guo, San Jose, CA (US)

(73) Assignee: LifeScan, Inc., Milpitas, CA (US)

( * ) Notice: Subject to any disclaimer, the term of this patent is extended or adjusted under 35 U.S.C. 154(b) by 157 days.

(21) Appl. No.: 09/974,597

(22) Filed: Oct. 10, 2001

(65) Prior Publication Data

US 2003/0098233 A1 May 29, 2003

(51) Int. Cl.[7] .................... G04N 27/327; G01R 27/26
(52) U.S. Cl. ............... 205/777.5; 205/775; 204/403.01; 324/658
(58) Field of Search ................ 205/777.5, 775, 205/788.5; 324/662, 663, 667, 671, 677, 678, 686, 425–437, 658, 664; 204/400–420

(56) References Cited

U.S. PATENT DOCUMENTS

| | | |
|---|---|---|
| 4,932,243 A | 6/1990 | Suh et al. |
| 5,628,890 A | 5/1997 | Carter et al. |
| 5,650,062 A | 7/1997 | Ikeda et al. |

FOREIGN PATENT DOCUMENTS

| | | | |
|---|---|---|---|
| WO | WO 87/03095 A1 * | 5/1987 | ......... G01N/33/566 |
| WO | WO 97/39343 * | 10/1997 | .......... G01N/27/22 |
| WO | WO 98/35225 | 8/1998 | ......... G01N/27/327 |
| WO | WO 99/32881 | 7/1999 | .......... G01N/27/26 |
| WO | WO 99/45387 | 9/1999 | ......... G01N/33/487 |
| WO | WO 99/47907 A1 * | 9/1999 | .......... G01N/11/00 |
| WO | WO 99/56613 | 11/1999 | ............ A61B/5/00 |
| WO | WO 00/20626 | 4/2000 | ............ C12Q/1/00 |
| WO | WO 01/33216 A1 | 5/2001 | ......... G01N/33/487 |

\* cited by examiner

*Primary Examiner*—Alex Noguerola
(74) *Attorney, Agent, or Firm*—Carol M. LaSalle; Bozicevic, Field & Francis, LLP

(57) ABSTRACT

Methods and systems are provided for determining whether a volume of biological sample is adequate to produce an accurate electrochemical analyte concentration measurement. Certain such methods and systems provide the additional function of compensating for a sample volume determined to be less than adequate in order to proceed with an accurate analyte concentration measurement. The present invention is employed with a biosensor, such as an electrochemical test strip to which the sample volume of biological solution is deposited, and a meter configured to receive such test strip and to measure the concentration of selected analytes within the biological sample.

34 Claims, 5 Drawing Sheets

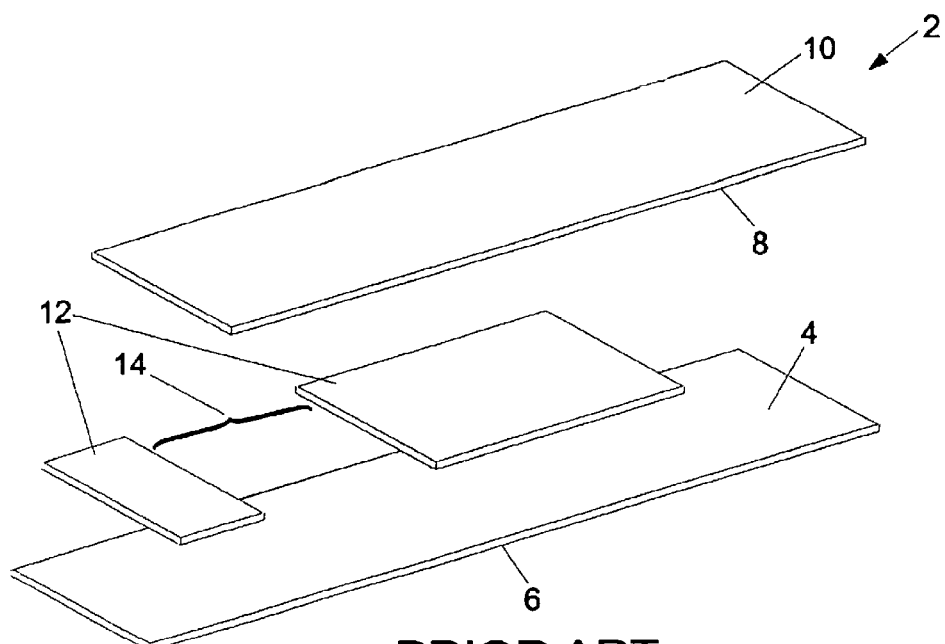
PRIOR ART
FIG._1
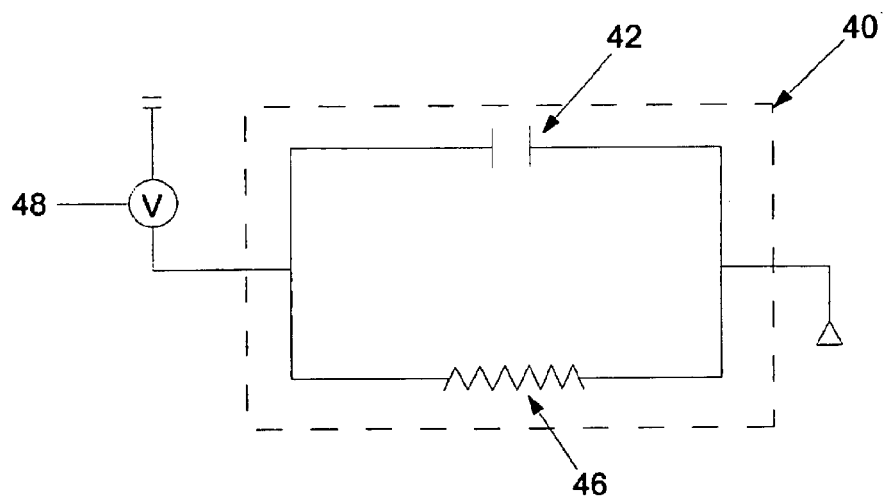
PRIOR ART
FIG._2

DETERMINATION OF SAMPLE VOLUME ADEQUACY IN BIOSENSOR DEVICES

FIELD OF THE INVENTION

The field of this invention is the electrochemical determination of analyte in biological fluids, particularly the electrochemical determination of the adequacy of the volume of the biological fluid sample to be tested for analyte concentration.

BACKGROUND OF THE INVENTION

Analyte concentration determination in biological fluids, e.g., blood or blood-derived products such as plasma, is of ever increasing importance to today's society. Such assays find use in a variety of applications and settings, including clinical laboratory testing, home testing, etc., where the results of such testing play a prominent role in the diagnosis and management of a variety of disease conditions. Common analytes of interest include glucose for diabetes management, cholesterol for monitoring cardiovascular conditions, and the like. In response to this growing importance of analyte concentration detection, a variety of analyte detection protocols and devices for both clinical and home use have been developed.

One type of method that is employed for analyte detection is an electrochemical-based method. In such methods, an aqueous liquid sample is placed into a reaction zone in an electrochemical cell made up of at least two electrodes, i.e., a counter/reference electrode and a working electrode, where the electrodes have an impedance which renders them suitable for amperometric measurement. The component to be analyzed, i.e., analyte, is allowed to react directly with an electrode, or directly or indirectly with a redox reagent to form an oxidisable (or reducible) substance in an amount corresponding to the concentration of the analyte. The quantity of the oxidisable (or reducible) substance present is then estimated electrochemically and related to the amount of analyte present in the initial sample.

Commonly, the electrochemical cell is in the form of a disposable test strip on which the biological sample is deposited and which is receivable within a meter by which the electrochemical analyte concentration measurement is made. Examples of assay systems that employ these types of test strips, often referred to as biosensors, and meters may be found in U.S. Pat. Nos. 5,942,102, 6,174,420 B1 and 6,179,979 B1, the disclosures of which are herein incorporated by reference. With these systems, determination of the concentration of an analyte in a biological sample first involves obtaining a biological sample and bringing that sample into contact with a reaction area of the test strip so that the biological sample, and more particularly the analyte of interest or derivative thereof, may react with the chemistry, e.g., the testing reagent(s), associated with the reaction area. In order to obtain an accurate measurement of the particular analyte(s) of interest, a minimum sample volume must be applied to the reaction area. It is not uncommon for an inadequate amount of sample volume to be provided, often due to user error or patient inexperience or misjudgment. Inaccurate measurements can result in a misdiagnosis or improper treatment, such as administering an inappropriate dosage of a drug, patient non-compliance, etc. Such can result in serious and even life-threatening consequences for those whose lives depend on frequent monitoring of an analyte in their body, for example, diabetics.

One approach to ensuring an adequate biological sample volume is to over-saturate or use a greater volume of sampled fluid than is necessary to fill the reaction area of the test strip. A disadvantage of using an unnecessarily large volume of a sampled fluid, a blood sample in particular, is the need to draw a greater volume of blood sample from the patient. This requires use of a blood sample volume, which is rather large, thus necessitating use of a larger diameter needle and/or deeper penetration into the skin. These factors can increase the discomfort and pain felt by the patient, and may be difficult to achieve for those individuals whose capillary blood does not readily express. As this sampling process may be repeated frequently within a single day, for many diabetics, for example, an increase in pain quickly becomes less tolerable or intolerable all together.

Some analyte detection biosensors have been developed to provide visual confirmation of the adequacy of sample volume, however, this feature does not exclude potential error by the patient in judging the adequacy of the sample's volume, e.g., diabetics may experience deteriorated vision. Certain other analyte determination biosensors do provide user-independent means for determining the adequacy of the sample volume. Examples of such biosensors are disclosed in U.S. Pat. Nos. 5,628,890 and 5,650,062 and PCT Patent Application Publication No. WO 99/32881 (PCT Patent Application No. PCT/US98/27203). In particular, the '881 publication describes an electrochemical glucose monitoring system which attempts to determine the adequacy of a volume of sample applied to a biosensor by applying a low-level AC voltage signal (without a DC voltage offset) at a known frequency to the biosensor and then measuring both the real component and the imaginary component of the resulting impedance. These impedance values are then compared to a look-up table in the microprocessor's program memory. The accuracy of this method may be additionally questionable considering that this system is dependent on blood hematocrit levels and environmental temperature variations.

Another disadvantage of the technique disclosed in the '881 publication is that the analyte measurement test must be aborted if the sample volume is determined to be inadequate, i.e., a "go-no-go" situation. This results in the need to take yet another sample from the patient which, as mentioned above, is inconvenient and may be very painful to the patient, likely resulting in patient non-compliance in his or her medication regime. Additionally, the test must be repeated resulting in the waste of test strips and increasing the cost of the procedure.

As such, there is continued interest in the identification of new techniques for accurately and precisely measuring the adequacy of the volume of the sample used for electrochemical analyte concentration determination. Of particular interest would be the development of methods that can very accurately and expeditiously determine the adequacy of the volume of sample. It would be additionally beneficial to develop such a sample volume adequacy determination technique in which a determination that a sample volume is inadequate does not require abortion of the analyte concentration measurement test. Ideally, this technique would compensate for the less than optimal sample volume and provide an accurate analyte concentration measurement without having to provide a new sample or conduct a new test.

SUMMARY OF THE INVENTION

The present invention provides methods and systems for measuring the volume of biological sample and determining whether such volume is adequate to produce an accurate measurement of at least one selected characteristic of the biological sample, such as the concentration of an analyte contained therein. Certain such methods and systems provide the additional function of compensating for a sample volume determined to be less than adequate in order to proceed with a measurement procedure.

The present invention is employed with a biosensor, such as an electrochemical test strip to which the sample volume of biological solution is deposited, and a meter configured to receive such test strip and to measure the concentration of selected analytes within the biological sample. The electrochemical test strip, as will be more fully described below, includes an electrochemical cell comprised of opposing electrodes between which a reaction zone is defined for receiving the biological sample, wherein the reaction zone has a defined thickness and volume.

When sufficient voltage is applied to an electrochemical cell, both double layer charging and electrochemical reaction will occur. As a consequence, charge flows to the electrodes of an electrical cell. The electrode-solution interface is analogous to that of a capacitor. The ratio of this charge to the voltage determines the capacitance of the electrode-solution interface. Since the total charge is due to the charging of the double layer and to the electrochemical reaction, two distinct capacitance components, $C_{dl}$ and $C_s$, respectively, contribute to the total or equivalent capacitance of the cell (see Bard, A. J. and Faulkner, L. R., Electrochemical Methods, 1980).

The inventors have discovered that the equivalent capacitance of an electrochemical cell is the most relevant factor in precisely determining sample volume, as the equivalent cell capacitance is linearly proportional to the amount of surface area of the cell electrodes in contact with the sample (the "covered cell area"), and thus, is linearly proportional to the volume of the sample within the cell, i.e., between the electrodes. The inventors have also discovered that the equivalent resistance of the electrochemical cell is additionally relevant in precisely determining sample volume, as the equivalent cell resistance is inversely proportional to the covered cell area, and thus, is inversely proportional to the sample volume.

Thus, a feature of the present invention is to derive such covered cell area and the corresponding sample volume from the equivalent cell capacitance or from both the equivalent cell capacitance and the equivalent cell resistance.

Another feature of the present invention is to control certain other factors (e.g., the thickness of the cell, the concentration of ionic species, etc.) that may interfere with accurately measuring sample volume in order that the value of the equivalent cell capacitance is independent and unaffected by the glucose concentration and blood hematocrit levels within the sample, the environmental temperature, particularities of the blood donor and other commonly interfering components of blood.

Yet another feature of the present invention is to provide the additional function of compensating for a sample volume determined to be less than adequate in order to proceed with an accurate analyte concentration measurement.

Accordingly, the present invention provides methods for determining the adequacy of the volume of a biological sample to be used for determining the concentration of one or more selected analytes within the donor sample, which achieves these objectives and provides these features.

In certain embodiments of the subject methods, an alternating current voltage (AC voltage) of low amplitude and having a selected frequency is applied to a biosensor containing the biological sample to be tested, thereby charging the biosensor. Optionally, a direct current voltage (DC voltage) may be applied simultaneously along with the AC voltage in order to increase the rate at which the capacitance of the biosensor becomes stabilized. The resulting alternating current generated from such charging is then measured, and the equivalent cell capacitance of the biosensor is then determined from the resulting alternating current. The equivalent cell capacitance is then used to determine the amount of surface area of the biosensor in contact with the sample solution, which surface area is then used to derive the volume of the sample within the biosensor. Upon a determination that the sample volume is adequate to make an accurate analyte concentration measurement, such analyte concentration is measured. On the other hand, if it is determined that the sample volume is inadequate, the subject methods may further include compensating for such inadequate sample volume during the analyte concentration measurement process. Inadequate volume compensation involves determining the necessary compensation factor which includes, at least in part, determining the ratio of the equivalent cell capacitance of the biosensor containing the actual sample volume to the cell capacitance of the biosensor when its entire available volume is filled.

The present invention also includes systems for carrying out the subject methods. The subject systems include electronic components and/or circuitry intended to be used with and electronically coupled to a biosensor, e.g., an electrochemical measurement cell in the form of, e.g., a disposable test strip, into which the sampled solution to be tested is deposited or is drawn by a capillary action. Most typically, such electronic circuitry is incorporated into a meter or other automated device configured to receive and operatively engage with such electrochemical cell, e.g., a disposable test strip, and to measure one or more physical or chemical characteristics of a biological sample held within the electrochemical cell. Most typically, such characteristics include the concentration of one or more target analytes within the biological sample. Such electronic circuitry may comprise discrete electronic components, e.g., a voltage supply, and/or integrated circuits having multiple circuit elements and/or semiconductor devices, e.g., a microprocessor suitably programmed to execute certain steps or functions of the subject methods based on certain signal or data inputs received from the electrochemical cell.

In certain embodiments, the systems of the present invention include such electronic circuitry and such an automated measurement device or meter, as just described, wherein the electronic circuitry is completely structurally and functionally integral with the automated measurement device.

While the subject methods and systems may be used to determine the sample volume of different biological samples, such as urine, tears, saliva, and the like, they are particularly suited for use in determining the sample volume of blood or blood fractions and the like. Furthermore, while the subject systems and methods for determining the sample volume in preparation for measuring a variety of physical and chemical characteristics of the sample, they are particularly useful in preparation for measuring the concentration of selected analytes within the sample.

These and other objects, advantages, and features of the invention will become apparent to those persons skilled in the art upon reading the details of the methods and systems of the present invention which are more fully described below.

BRIEF DESCRIPTION OF THE DRAWINGS

FIG. 1 is an exploded view of an exemplary conventional electrochemical test strip for electrochemical analyte concentration determination, which is usable with the present invention.

FIG. 2 is a schematic illustration of a circuit representative of the equivalent cell impedance of the test strip of FIG. 1.

DETAILED DESCRIPTION OF THE PREFERRED EMBODIMENTS

Figure 3:
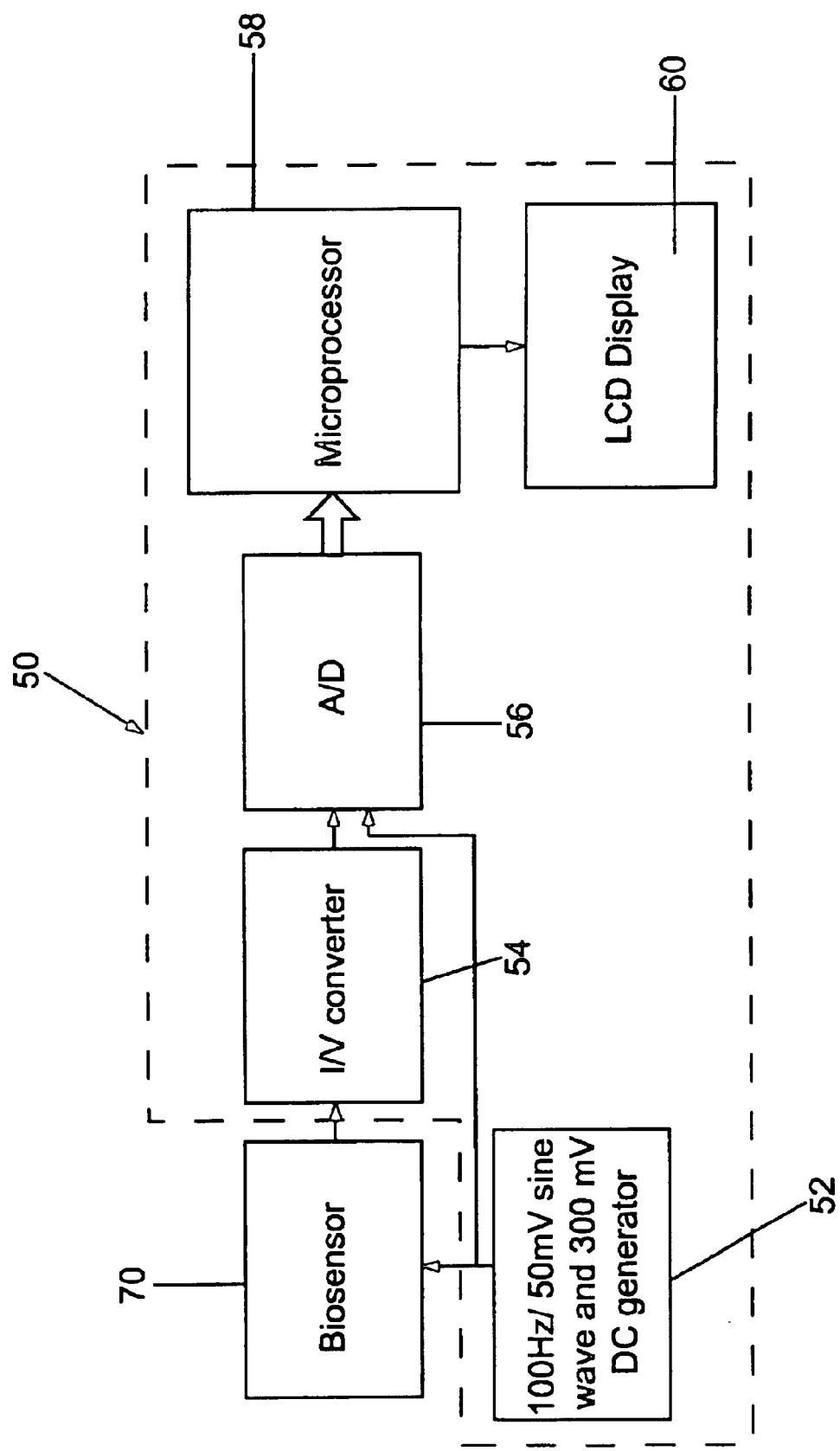
FIG. 3 is a block diagram illustration of a system of the present invention operatively coupled to an electrochemical biosensor for measuring the equivalent cell capacitance of the electrochemical biosensor when a voltage is applied to the biosensor.

The present invention provides systems and methods for determining the volume of a biological sample for purposes of measuring a selected characteristic of the sample, e.g., analyte concentration, and determining whether such volume is adequate to produce an accurate measurement of such selected characteristic. Certain such systems and methods provide the additional function of compensating for a sample volume determined to be less than adequate in order to provide an accurate measurement of such characteristic.

Before the present invention is described in further detail, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publications provided may differ from the actual publication dates, which may need to be independently confirmed.

Definitions

The term "double layer" as used herein refers to the whole array of charged species and oriented dipoles existing at the interface between an electrode surface and a solution, e.g., a sample of a biological solution, in contact with the electrode surface when a voltage is applied to the electrode.

The term "double layer capacitance," $C_{dl}$, as used herein means the capacitance contributed by the charging of the double layer of the electrode-solution interface.

The term "Faradaic capacitance," $C_s$, as used herein refers to the pseudocapacitance component due to the electrochemical reaction process that occurs on the electrode surface.

The term "Faradic current," $i_F$, as used herein means the current or electron transfer that occurs at the surface of an electrode to which a voltage has been applied.

The term "equivalent cell capacitance," C, when used herein in reference to an electrochemical cell means the total equivalent capacitance across the electrochemical cell, which results when a voltage has been applied to the electrochemical cell. The equivalent cell capacitance is dominated by the double layer capacitance and the Faradaic capacitance.

The term "equivalent cell resistance," R, as used herein in reference to an electrochemical cell means the total equivalent resistance across the electrochemical cell, which results when a voltage has been applied to electrochemical cell.

The "equivalent cell impedance," Z, as used interchangeably herein in reference to an electronic circuit or component, e.g., an electrochemical cell, means the total impedance of the circuit including but not necessarily limited to the combination of the equivalent cell capacitance and the equivalent cell resistance, which results when a voltage has been applied to the electrochemical cell.

The term "Faradaic current," $i_F$, as used herein, means the current resulting from electron transfer between sample component and surface of an electrode as a result of electrochemical reaction when a voltage has been applied.

The terms "derive," "determine," "calculate," and the like, and their respective derivatives, are used interchangeably herein.

The present invention will now be described in detail. In further describing the present invention, exemplary electrochemical biosensors, usable with the systems and employable by the methods of the present invention, will be described first, followed by a detailed description of the subject methods and systems, as well as a description of the subject kits that include the subject systems for use in practicing the subject methods.

Electrochemical Biosensors

As summarized above, the invention provides methods and systems for measuring the volume of a sample of biological material used for analyte concentration measurement and determining whether such volume is adequate to produce an accurate analyte concentration measurement. These methods and systems are usable with a biosensor, more particularly an electrochemical cell-based biosensor, into which the sampled biological material is deposited or transferred. There are varying designs of electrochemical cell-based biosensors. The most common of these designs employed in the field of analyte concentration monitoring include test strip configurations, such as those disclosed in U.S. Pat. No. 6,193,873 and in copending U.S. patent application Ser. Nos. 09/497,304; 09/497,269; 09/736,788 and 09/746,116, the disclosures of which are herein incorporated by reference. Such test strips are used with meters configured for electrochemical measurements, such as those disclosed in the above-identified patent references.

Electrochemical biosensors other than test strips may also be suitable for use with the present invention. For example, the electrochemical cell may have a cylindrical configuration wherein a core electrode is co-axially positioned within a second tubular electrode. Such electrochemical cell configurations may be in the form of micro-needles and, as such, are either integral within the needle structure for in situ (e.g., typically under the skin surface) measurements or otherwise in physical or fluid communication with a micro-needle structure. Examples of such micro-needle are disclosed in copending U.S. patent application Ser. Nos. 09/878,742 and 09/879,106 filed on Jun. 12, 2001, hereby incorporated by reference. For purposes of this disclosure, the subject devices will be described in use with electrochemical cells in test strip configurations; however, those skilled in the art will appreciate that the subject devices may be used with any suitable electrochemical cell configuration, including micro-needle configurations.

The type of electrochemical measurement that is made may vary depending on the particular nature of the assay and the meter with which the electrochemical test strip is employed, e.g., depending on whether the assay is coulometric, amperometric or potentiometric. The electrochemical cell will measure charge in a coulometric assay, current in an amperometric assay and potential in a potentiometric assay. For purposes of this disclosure, the present invention will be described in the context of amperometric assays; however, the subject devices may be employed with any type of assay and electrochemical measurement.

Generally, in any configuration, an electrochemical cell includes at least two electrodes spaced-apart in either a facing arrangement or in a side-by-side arrangement in the same plane. In the first arrangement, the electrodes are separated by a thin spacer layer, which defines a reaction area or zone, or chamber into which a biological sample is deposited or transferred for analyte concentration measurement. In the side-by-side configuration, the electrodes are in a chamber with a defined thickness and volume. Present in the reaction area or chamber, i.e., coated on one or more of the facing surfaces of the electrodes, are one or more redox reagents selected to chemically react the target analyte(s). Such redox reagents typically comprise at least one enzyme and a mediator.

A representation of an exemplary conventional electrochemical test strip 2 suitable for use with the present invention is provided in the exploded view of FIG. 1. Test strip 2 is made up of a two electrodes 4, 8 separated by a spacer layer 12 which has a cutaway section that defines the reaction zone or area 14. Generally, the electrodes 4, 8 are configured in the form of elongated rectangular strips each having a length in the range from about 2 to 6 cm, usually from about 3 to 4 cm, having a width in the range from about 0.3 to 1.0 cm, usually from about 0.5 to 0.7 cm, and having a thickness in the range from about 0.2 to 1.2 mm, and usually from 0.38 to 0.64 mm.

The surfaces of electrodes 4, 8 that face the reaction area in the strip is made of a conductive material, preferably a metal, where metals of interest include palladium, gold, platinum, iridium, doped indium tin oxide, stainless steel, carbon and the like. The outside surfaces 6, 10 of electrodes 4, 8 are made of an inert support or backing material. Any suitable inert backing material may be used with electrodes 4, 8, where typically the material is a rigid material that is capable of providing structural support to the electrode and, in turn, the electrochemical test strip as a whole. Such suitable materials include plastics, e.g., PET, PETG, polyimide, polycarbonate, polystyrene, silicon, ceramic, glass, and the like. Electrodes 4, 8 and test strip 2 may be fabricated using any of various manufacturing techniques known to those skilled in the relevant art.

As described above, a thin spacer layer 12 is positioned or sandwiched between electrodes 4, 8. The thickness of spacer layer 12 generally ranges from about 1 to 500 $\mu$m, and usually from about 50 to 150 $\mu$m. Spacer layer 12 may be fabricated from any convenient material, where representative suitable materials include PET, PETG, polyimide, polycarbonate and the like. The surfaces of spacer layer 12 may be treated so as to be adhesive with respective electrodes 4, 8 and thereby maintain the structure of the electrochemical test strip 2.

Spacer layer 12 is cut so as to provide a reaction zone or area 14 having any appropriate shape including circular, square, triangular, rectangular, or irregular shaped reaction areas. The top and bottom of the reaction zone 14 is defined by the facing surfaces of electrodes 4, 8 while spacer layer 12 defines the side walls of the reaction area 14. The volume of the reaction area ranges from at least about 0.1 to 10 $\mu$l, usually from about 0.2 to 5.0 $\mu$L and more usually from about 0.3 to 1.6 $\mu$L.

Present in the reaction area 14 is a redox reagent system, which reagent system provides for the species that is detected by the electrode and therefore is used to derive the concentration of analyte in a biological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Typical enzymes of interest include oxidoreductases, hydrolases, transferases and the like; however, the specific enzyme present in the reaction area depends on the particular analyte for which the electrochemical test strip is designed to detect. Where the analyte of interest is glucose, for example, suitable enzymes include glucose oxidase, glucose dehydrogenase (either β-nicotineamide adennine dinucleotide based (NAD) or 4,5-Dihydro-4,5-dioxo-1H-pyrrolo[2,3-f]quinoline-2,7,9- tricarboxylic acid based (PQQ)). Where the analyte is cholesterol, suitable enzymes include cholesterol esterase and cholesterol oxidase. For other analytes, enzymes including but not limited to lipoprotein lipase, glycerol kinase, glycerol-3-phosphate oxidase, lactate oxidase, lactate dehydrogenase, pyruvate oxidase, alcohol oxidase, bilirubin oxidase, uricase, and the like may be used.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose is the analyte of interest and glucose oxidase or glucose dehydrogenase is the enzyme components, mediator of particular interest is ferricyanide. Other reagents that may be present in the reaction area include buffering agents, e.g., citraconate, citrate, phosphate, "Good" buffers and the like.

The redox reagent system is generally present in dry form. The amounts of the various components may vary, where the amount of enzyme component typically ranges from about 0.1 to 20% by weight.

Methods of the Present Invention

As summarized above, the subject invention includes methods for determining the volume of biological sample deposited or transferred to an electrochemical cell having a reaction zone or chamber with a defined volume and determining whether such volume is adequate to produce an accurate analyte concentration measurement. As mentioned above, a feature of the subject methods in determining sample volume is the determination of the equivalent capacitance of the cell, as well as the equivalent cell resistance. As such, the subject methods provide a more accurate measure of sample volume than that which has been achieved by the prior art.

Another feature of the subject methods in determining the equivalent cell capacitance and resistance and sample volume is to disregard certain characteristics or factors of the sampled solution or ambient conditions which either have no affect on the determination of the equivalent capacitance and/or equivalent resistance or are otherwise strictly controlled so as not to have such an affect. Such factors which are controlled or independent of the equivalent capacitance include but are not limited to the concentration of ionic species, blood hematocrit, blood glucose concentration, environmental temperature, the blood donor, and sensor interferences typically found in blood, cell thickness and biosensor aging.

For purposes of understanding the description of the subject methods, a simplified model of an impedance circuit 40 of the electrochemical cell of the test strip of FIG. 1 is provided in FIG. 2. Impedance circuit 40 is representative of the impedance factors of the test strip when containing a sample of biological solution and having a voltage applied to it. When both AC and DC voltages are applied to the cell, impedance circuit 40 comprises equivalent cell capacitance (C) 42, which includes the double layer and the Faradaic capacitances, and the equivalent cell resistance (R) 46 of the electrochemical cell.

Prior to practicing the subject methods, it is first necessary to obtain the biological sample to be measured and placing such sample within the test strip cell. Placement of the sample within the test strip may be accomplished by first inserting the test strip into the test meter and then applying the sample to the test strip ("on-meter dosing"), or by first applying the sample to the test strip and then inserting the test strip into the test meter ("off-meter dosing"). The latter sequence is often preferred in hospital environments as it is more likely to cross-contamination within the meter. The measurement meter then detects that the biological sample has been introduced into the electrochemical cell (as disclosed in U.S. Pat. No. 6,193,873).

Once such sample is detected, the first step of the subject methods is to apply an alternating voltage ($V_{AC}$) of low amplitude to the biosensor. The amplitude of the applied AC voltage is selected such that its application does not result in a Faradaic current ($i_F$), i.e., the electron transfer that occurs at the electrode surface as result of electrochemical reaction upon application of a voltage to the electrode. As such, the amplitude of the applied AC voltage is in the range from about 2 to 100 mV rms, typically is in the range from about 5 to 75 mV rms, and more typically is about 50 mV rms. The frequency (f) of the applied AC voltage is also selected so as to maximize the signal to noise ratio (i.e., the ratio of the measured equivalent cell capacitance to the variability in the measured equivalent cell capacitance) of the cell. As such, an acceptable frequency of the applied AC voltage is in the range from about 50 to 10,000 Hz, typically in the range from about 75 to 1,000 Hz, and more typically is about 100 Hz.

Optionally, a DC voltage may be applied to the biosensor, either simultaneously with the AC voltage or fractions of a second prior to application of the AC voltage This DC voltage is generally in the range from about 0 to 600 mV, typically from about 200 to 500 mV and more typically from 300 to 400 mV. The DC voltage component causes the electrochemical cell equivalent capacitance to stabilize more rapidly than it would with an AC voltage alone. The rapid stabilization of the cell capacitance allows a determination of the sample volume before commencing the analyte measurement, thus minimizing overall testing time.

After application of the AC and DC voltages, the alternating current ($i_{AC}$) generated from charging the electrochemical cell is then measured. The equivalent cell capacitance of the biosensor can then be determined from the amplitude and the phase of the resulting alternating current.

For the equivalent cell capacitance to depend only on the cell surface area contacted by biological sample, the charge separation distance ($d_{dl}$) of the double layer capacitance must be strictly controlled such that it is constant during the determination of the volume of the sample solution. The thickness of the double layer capacitor is dependent on the applied voltage, concentrations of the charged species in the solution. In order to ensure a constant thickness of the charge separation layer, and thus ensure an accurate determination of the surface area of each electrode in contact with the sample solution and an accurate determination of the sample volume, the ion concentration of the redox reagent is strictly controlled, while the ion concentration of the sample is physiologically controlled in a very narrow range.

As mentioned above, the equivalent resistance of the electrochemical cell is additionally relevant to accurately determining sample volume. Thus, establishing that the equivalent cell resistance (R) is inversely proportional to the surface area of the cell covered by the sample and that the equivalent cell capacitance (C) is linearly proportional to the covered cell area, as represented by the following relationships:

$$R = \rho l/A \text{ and } C \propto A$$

where $\rho$ is the resistivity of the electrochemical cell, l is the length of the cell electrode, and A is the conducting surface area of the cell, the following relationship exists:

$$C/R \propto A^2$$

Thus, the amount of surface area of the cell covered by the biological sample can be determined by the ratio of the equivalent cell capacitance to the equivalent cell resistance. By taking into consideration the effect of sample volume on two impedance components (capacitance and resistance) of the cell rather than just on one of them (e.g., capacitance), a relationship is established which offers more sensitivity in response to the variations in the amount of cell surface area covered by a biological sample. More specifically, the ratio of the cell capacitance to cell resistance provides a quadratic relationship rather than a linear relationship with respect to the surface area of the cell covered by a biological sample, thus increasing the sensitivity in the measured change(s) to the covered cell area. Therefore, the determination of the covered cell area according to this method is even more accurate than when only the equivalent cell capacitance is considered.

Upon a determination of the surface area of the electrode in contact with or covered by the sample solution, the volume ($V_S$) of the sample solution within the biosensor, i.e., within the reaction zone of the electrochemical cell, can then be determined according to the following equation:

$$V_S = A \cdot d$$

where d is the distance between the cell electrodes in a facing electrode configuration or the depth of the cell in a side-to-side electrode configuration.

A determination is then made as to whether the volume of the sample provided to the test strip is adequate to proceed with the analyte concentration measurement. Such a determination is made by comparing the calculated sample volume with the total volume of the electrochemical cell. As is discussed in more detail below with respect to the systems of the present invention, certain parameters including but not limited to the value of the total cell volume, operating temperature range, proper test strip insertion into the meter, among other data (both static and dynamic) or parameters related to the particular cell, are stored in the memory of a microprocessor, for example, upon calibration of the meter and other related components of the subject systems.

If the sample volume is determined to be adequate, measurement of the desired characteristic, e.g., an analyte concentration, is made, the results of which may be displayed on a display unit, described in more detail below with respect to the subject systems. On the other hand, if the sample volume is determined to be inadequate, i.e., too low, to provide an accurate measurement, the display unit may be configured to display a low volume icon.

As discussed above, certain embodiments of the subject methods include the additional function of compensating for an inadequate sample solution volume in order to make an accurate measurement of the selected characteristic, e.g., concentration of the targeted analyte(s), without having to redo the sampling and testing steps.

It is known in the art that the concentration of a selected analyte, such as glucose, of the biological sample within the cell is proportional to the Faradaic current ($I_F$) that is passed through the electrochemical cell when a DC voltage is applied, that the cell current is proportional to the cell surface area covered by the sample solution. As mentioned above, the inventors have determined that such surface area is proportional to the equivalent capacitance of the cell. Thus, the concentration of the selected analyte is proportional to the equivalent cell capacitance. By determining the equivalent cell capacitance when a sample solution is present and by knowing the capacitance of the cell when completely filled with a biological solution (determined by a calibration process), the compensation factor ($F_{cf}$) necessary to compensate for a low sample volume and to provide an accurate analyte concentration measurement can be determined according to the following equation:

$$F_{cf} = C_f / C_{pf}$$

where $C_f$ is the equivalent capacitance of the completely filled electrochemical cell and $C_{pf}$ is the equivalent capacitance of the electrochemical cell containing the inadequate volume of biological sample. The corrected analyte concentration measurement (G) is then made with the appropriate compensation factor ($F_{cf}$) according to the following equation:

$$G = F_{cf} G_{pf}$$

where $G_{pf}$ is the analyte concentration calculated from the cell containing inadequate volume of biological sample. In being able to compensate for inadequately low sample volume, the subject methods avoid wasting test strips, decrease costs and reduce the time necessary for conducting the analyte measurement.

Thus, generally summarized in accordance with the above principles and discoveries, certain methods of the present invention include the steps of applying an AC voltage having a selected amplitude and a selected frequency to the biosensor with or without also applying a DC voltage to the biosensor; measuring the AC current generated by application of the voltage(s); determining the capacitance or both the capacitance and the resistance of the biosensor from the measured AC current; determining the surface area of the portion of the biosensor in contact with the sample based on the determined capacitance or based on both the determined capacitance and the determined resistance; and then determining the volume of the sample within the biosensor based on the determined surface area.

Other subject methods further include the step of measuring one or more physical or chemical characteristics of the biological sample, such as the concentration of one or more selected analytes, based on a determination that the sample volume is adequate. Still other subject methods include compensating for an inadequate volume of a biological sample held within an electrochemical biosensor for measurement of at least one characteristic of the biological sample in order to accurately measure the value of the characteristic. Such compensation method includes determining the necessary compensation factor to compensate for an inadequate sample volume if such is determined, and thereafter compensating for the inadequate sample volume while measuring, for example, the concentration of a selected analyte present within the sample. The step of determining the necessary compensation factor includes determining the ratio of the equivalent capacitance of the biosensor when completely filled with the sample to the determined equivalent capacitance of the biosensor with the inadequate sample volume. The value of the equivalent capacitance of the biosensor when completely filled within said sample may be accessed from a memory storage means.

Systems of the Present Invention

The present invention also provides systems for practicing the above-described subject methods. Generally described, such a system may include the following components for carrying out the steps of the above-described methods of the present invention: a voltage supply configured for applying a voltage to the electrochemical cell, means for measuring a current generated by the cell when the voltage is applied to the cell, means for deriving the capacitance and/or resistance of the cell from the measured current; means for deriving the surface area of the cell covered by the biological sample from the cell capacitance and/or resistance; and means for deriving the volume of the biological sample from the cell surface area. Certain systems further include means for determining whether the sample volume is adequate for making an accurate measurement of one or more selected characteristics of the biological sample, including but not limited to the concentration of one or more selected analytes within the biological sample. Certain of these systems further include means for compensating for an inadequate sample volume while the selected characteristic of the biological sample.

FIG. 3 illustrates a block diagram of an exemplary system 50 of the present invention. System 50 includes electronic components and circuitry configured to be electronically coupled to a biosensor 70, e.g., an electrochemical measurement cell in the form of a disposable test strip as described above with respect to FIG. 1, into which the sampled biological solution to be tested is deposited or transferred. More particularly, system 50 includes a voltage supply 52 for supplying the requisite AC and DC input voltages to biosensor 70. System 50 further includes a current-to-voltage converter 54, an analog to digital converter 56 and a microprocessor 58, which collectively act to receive and process data from biosensor 70. In particular, current-to-voltage converter 54 is operatively coupled to an output terminal of biosensor 70 for receiving the output current signal from biosensor 70 when a voltage is applied by voltage supply 52 and for converting that current signal to a corresponding voltage signal. This corresponding voltage signal is then provided as an input to analog-to-digital converter 56 which converts the analog voltage signal to a corresponding digital value. This digital voltage value is then provided as an input signal to microprocessor 54 which is programmed to derive and/or determine the factors or parameters of interest, e.g., equivalent cell capacitance, equivalent cell resistance, the surface area of the biosensor in contact with the biosensor, the volume of the biological sample, the volume compensation factor, etc.; and to control the timing of each of these functions. As previously mentioned, microprocessor 54 may include a memory storage means for storing predetermined, preselected or calibrated data or information such as the total volume of the electrochemical cell, calibration parameters, operating temperature range, sample type information, sample detection information and the like which are necessary or useful for performing the steps and functions of the subject methods. Although a microprocessor has been described for purposes of storing and processing data in accordance with the principles of the present invention, those skilled in the art will recognize that other discrete electronic components may be collectively configured to achieve the objectives of the present invention.

The subject system may further include a display device or unit 60 for displaying selected empirical or symbolic data, information or outputs supplied by the control device or microprocessor. Such data, information or outputs may include, but are not limited to, measured or derived values of selected output signals and impedance factors, sample volume size, volume adequacy/inadequacy indicator icons, inadequate volume compensation factors, concentrations of analytes of interest, biological sample versus control sample indicator icons, calibration results, etc.

In many embodiments, the electrochemical signal application, measurement, derivation, calculation, compensation and display steps, as described above, are performed automatically by the subject systems designed to work with the electrochemical cell. As such, the electronic circuitry of the subject systems may be structurally and functionally integrated into a meter or other automated device configured to receive and operatively engage with an electrochemical cell, e.g., a disposable test strip, and to measure one or more physical or chemical characteristics of a biological sample held within the electrochemical cell. Most typically, such characteristics include the concentration of one or more target analytes within the biological sample. A representative meter or device for automatically practicing some of the same or similar steps and functions, such that the user need only apply a biological sample to the reaction zone of an electrochemical cell and then read the final analyte concentration result from the device, is further described in U.S. Pat. No. 6,193,873 B1, the disclosure of which is herein incorporated by reference.

Those skilled in the relevant art will appreciate that the subject systems are usable with assay systems that do not comprise biosensors of the type described above. Such other systems include, for example, an electrochemical cell having at least two electrodes and a redox reagent system having a fixed concentration of ions, wherein the electrodes are configured to be placed within a biological sample or environment having a fixed concentration of ions.

EXAMPLES

The following results have been observed in connection with the present invention. FIGS. 4–8 illustrate the variation in the experimental results of measurements made of test strips having an adequate sample volume (i.e., test strips having reaction zones completely filled with sample solution or material) and of test strips having less than an adequate sample volume (i.e., test strips having reaction zones half filled with sample solution or material). More particularly, measurements of the equivalent capacitance of the electrochemical cells and the sample solution resistance were made over selected periods of time during which the appropriate voltages were applied to the test strips. The following experimental results are offered by way of illustration and not by way of limitation. The results illustrated were collected by dosing the strips with 5 different blood donors, glucose range of 40–600 mg/dL, hematocrit of 20% and 70%, at room temperature.

Figure 4:
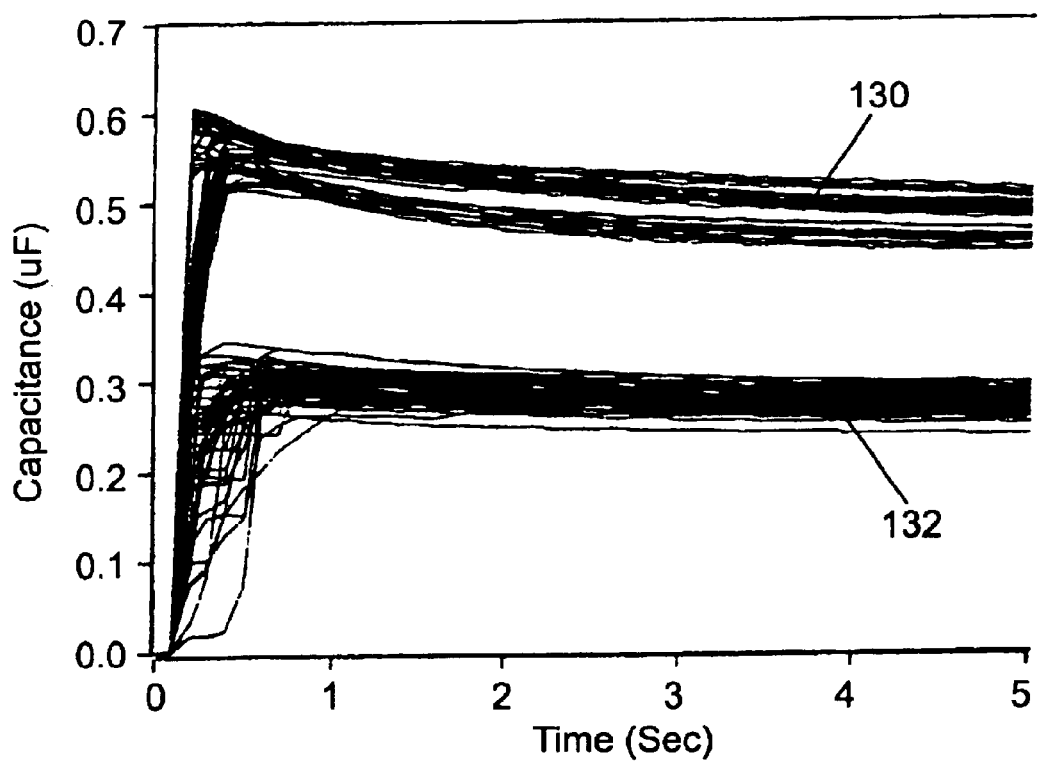
FIG. 4 is a graph depicting the relationship of the change in the equivalent cell capacitance (y-axis) over time (x-axis) of the electrochemical cell of the test strip of FIG. 1 when the cell is completely filled and half filled, respectively, with a sampled solution.

FIG. 4 illustrates a comparison of the change in the equivalent cell capacitance (y-axis) over time (x-axis) of test strips 130 completely filled with blood samples and test strips 132 half-filled with blood samples. The graph shows that the completely filled test strips 130 produced an equivalent cell capacitance twice as great as the equivalent capacitance of the half-filled test strips 132.

Figure 5:
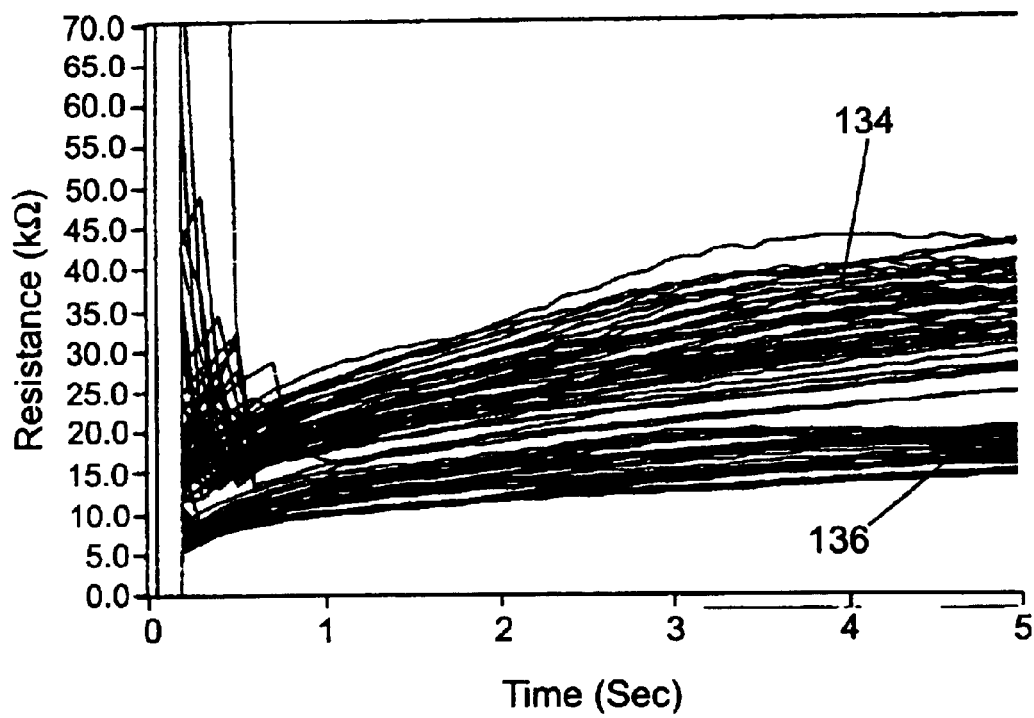
FIG. 5 is a graph depicting the relationship of the change in the equivalent resistance (y-axis) of the electrochemical over time (x-axis) when the cell of the test strip of FIG. 1 is completely filled and half filled, respectively, with a sampled solution.

FIG. 5 illustrates a comparison in the change in the equivalent cell resistance (y-axis) over time (x-axis) in test strips 136 completely filled with the blood samples and test strips 134 half-filled with the blood samples. The graph shows that the greater volume of blood sample produced an equivalent cell resistance about one half of that of the test strips filled with the smaller volume of blood sample.

Figure 6:
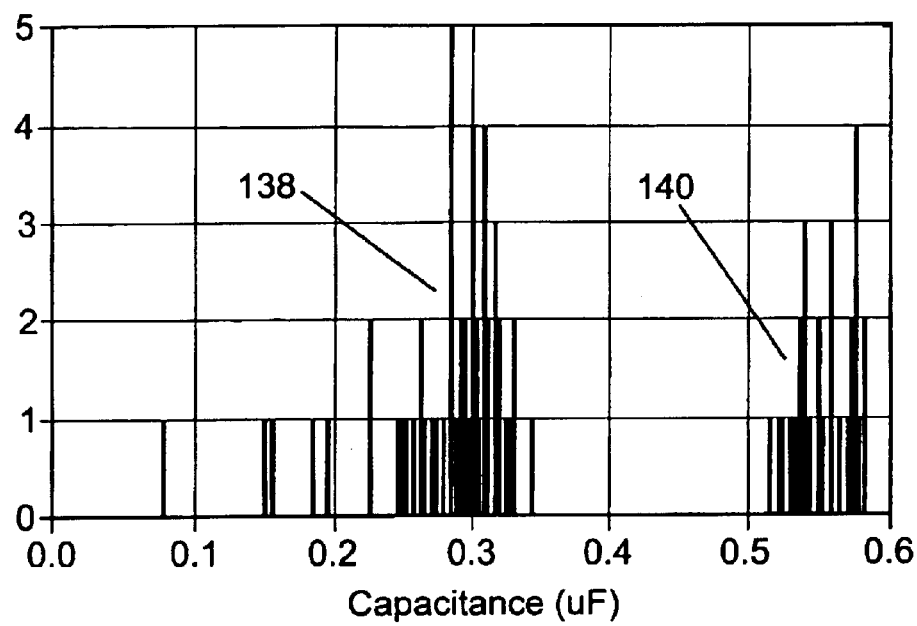
FIG. 6 is a histogram depicting the relationship of the change in the equivalent cell capacitance (x-axis) of the electrochemical cell of the test strip of FIG. 1 at 0.5 seconds after application of the sample solution to the test strip (y-axis) when the cell is completely filled and half filled, respectively, with a sampled solution.

FIG. 6 illustrates histograms of the equivalent cell capacitance (x-axis) of test strips 140 completely filled with blood samples and test strips 138 half-filled with blood samples, wherein the equivalent cell capacitance is measured at 0.5 seconds after blood sample is applied to the test strip. The graph shows that the completely filled test strips 140 produced an equivalent cell capacitance twice as great as the equivalent capacitance of the half-filled test strips 138 with a very good reproducibility.

Figure 7:
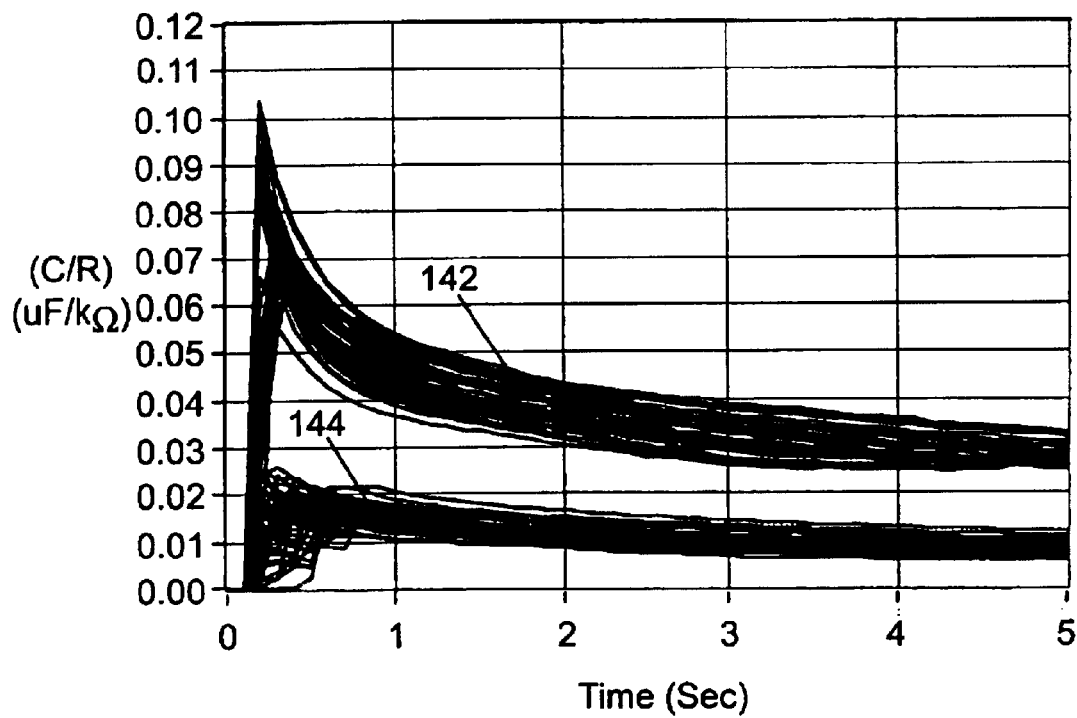
FIG. 7 is a graph depicting the ratio of the equivalent cell capacitance and the equivalent cell resistance (y-axis) over time (x-axis) when the electrochemical cell of the test strip of FIG. 1 is completely filled and half filled, respectively, with a sampled solution.

FIG. 7 illustrates a comparison of the change in the ratio of the equivalent cell capacitance to the equivalent cell resistance (C/R) (y-axis) over time (x-axis) of test strips 142 completely filled with blood samples and test strips 144 half-filled with blood samples. The graph shows that the completely filled test strips 142 produced a C/R about four times as great as the C/R of the half-filled test strips 144.

Figure 8:
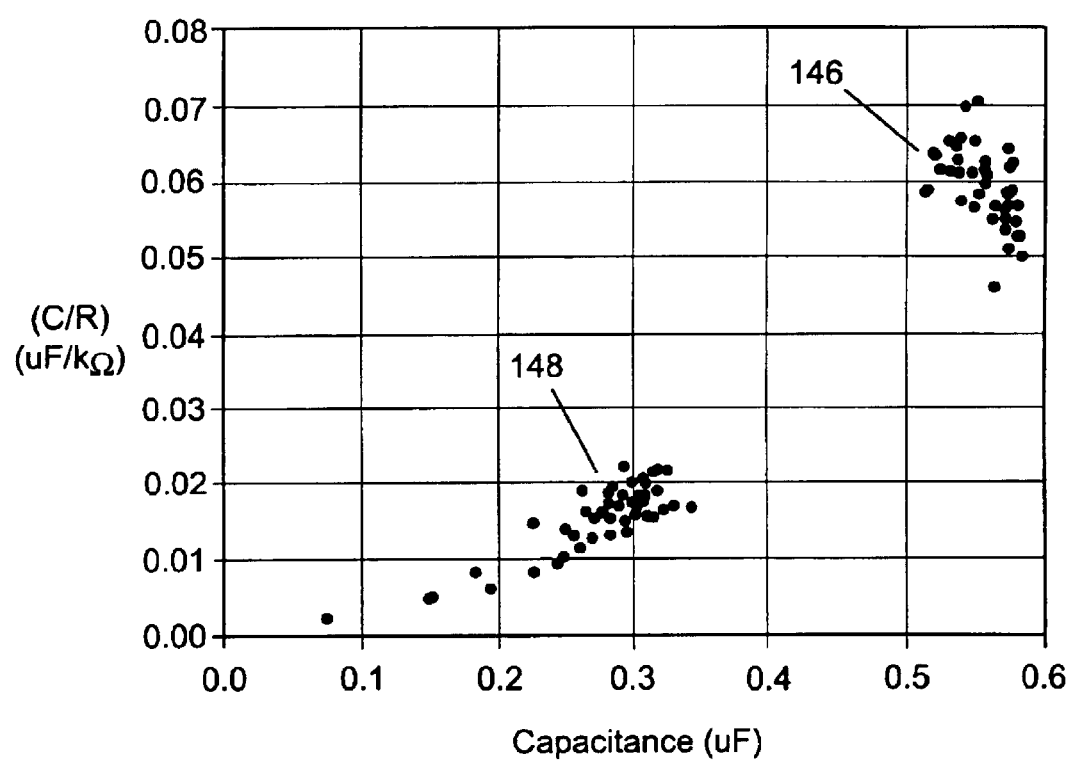
FIG. 8 is a scatter diagram of the ratio of the equivalent cell capacitance and the equivalent cell resistance (y-axis) versus the equivalent cell capacitance (x-axis) measured at 0.5 seconds following sample application when the electrochemical cell is completely filled and half filled, respectively, with a sampled solution.

FIG. 8 illustrates a comparison of a scatter diagram of the ratio of the equivalent cell capacitance to the equivalent cell resistance (C/R) (y-axis) versus the equivalent cell capacitance (x-axis) of test strips 146 completely filled with blood samples and test strips 148 half-filled with blood samples, wherein the capacitance and the resistance are measured at 0.5 seconds after application the blood sample to the test strip. The graph shows that C/R produced more sensitivity to the sample volume compared to the equivalent cell capacitance C.

Kits

Also provided by the subject invention are kits for use in practicing the subject methods. The kits of the subject invention include a subject system including the electronic circuitry, as described above, or in the form of a meter or other automated instrument, as described above, for determining whether the volume of sample applied to a test strip is adequate enough to provide an accurate analyte concentration measurement to be made. In certain other kits, the subject systems also compensate for such inadequate volume when making an analyte concentration measurement. The kits may further include instructions for using the subject systems according to the subject methods with an electrochemical cell, in the form of a test strip or microneedle or the like, in the determination of the volume of a sampled solution or material held within the electrochemical cell. These instructions may be present on one or more of the packaging, a label insert, and the like.

It is evident from the above description that the features of the subject methods and systems overcome many of the disadvantages of prior art techniques for determining the volume of a biological sample deposited on a test strip for electrochemical analyte concentration analysis, and provide certain advantages including, but not limited to, providing a very accurate means and technique for making such sample volume determination and decreasing the time necessary to conduct analyte concentration measurements. Further, such sample volume determination is not subject to variations of blood glucose concentration, blood hematocrit level, the blood donor, testing temperature, and the concentration of interferences often present in blood samples. Other advantages of the invention include the ability to compensate for an inadequate sample volume and proceed with the analyte concentration measurement without having to abort the testing procedure, minimizing waste and costs. As such, the subject invention represents a significant contribution to the field of fluid of biological sample volume determination and analyte concentration measurement.

The subject invention is shown and described herein in what is considered to be the most practical and preferred embodiments. It is recognized, however, that departures may be made there from, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A method for determining the volume of a biological sample held within an electrochemical biosensor, comprising:

applying an alternating voltage having a selected amplitude and a selected frequency to the biosensor;

measuring the current generated by applying said alternating voltage;

determining the capacitance of the biosensor from said measured current;

determining the surface area of the biosensor in contact with the sample based on said determined capacitance; and determining the volume of the sample within the biosensor based on said determined surface area.

2. The method of claim 1 further comprising determining whether said sample volume is adequate for measuring one or more selected characteristics of said sample.

3. The method of claim 2 further comprising measuring the concentration of one or more selected analytes present within said sample after a determination that said sample volume is adequate.

4. The method of claim 2 further comprising measuring the concentration of one or more selected analytes present within said sample after a determination that said sample volume is inadequate said measuring comprising:

determining the necessary compensation factor to compensate for said inadequate volume in order to accurately measure the at least one analyte concentration; and compensating for said inadequate sample volume.

5. The method of claim 4 wherein determining the necessary compensation factor comprises determining the ratio of the capacitance of the biosensor when completely filled with said sample volume to the capacitance of the biosensor with said inadequate sample volume.

6. The method of claim 1 further comprising determining the resistance of the biosensor from said measured current.

7. The method of claim 6 further comprising determining the surface area of the biosensor in contact with the sample based on said determined capacitance and said determined resistance.

8. The method of claim 1 further comprising applying a direct current voltage to said biosensor.

9. The method of claim 8 wherein said direct current voltage and said alternating current voltage are applied simultaneously.

10. The method of claim 8 wherein said direct current voltage is in the range from about 0 to 600 mV.

11. The method of claim 1 wherein said electrochemical biosensor comprises at least two electrodes forming an electrochemical cell having a cell volume and wherein said determined surface area is a surface area of said at least two electrodes covered by said biological sample.

12. The method of claim 1 wherein said amplitude of the applied alternating voltage is selected such that it does not result in a Faradic current within the biosensor.

13. The method of claim 12 said amplitude is the range from about 2 to 100 mV rms.

14. The method of claim 13 wherein said amplitude is about 50 mV rms.

15. The method of claim 1 wherein said frequency of said applied alternating voltage is selected such that the ratio of the equivalent cell capacitance to the variability of the equivalent cell capacitance of the biosensor is maximized.

16. The method of claim 15 wherein said frequency is in the range from about 50 to 10,000 Hz.

17. The method of claim 16 wherein said frequency is about 100 Hz.

18. A method for measuring at least one characteristic of a biological sample held within an electrochemical biosensor, comprising:
   determining the volume of said biological sample held within said electrochemical biosensor;
   determining the adequacy of the volume of said biological sample for measuring said at least one characteristic; and
   upon determining that said volume of said biological sample is inadequate, compensating said at least one characteristic measurement for said inadequate volume.

19. The method of claim 18 wherein said at least one characteristic is the concentration of one or more selected analytes present within said sample.

20. The method of claim 18 wherein said compensating for an inadequate volume comprises determining the ratio of the capacitance of the biosensor when completely filled with said sample to the capacitance of the biosensor with said inadequate sample volume.

21. The method of claim 20 wherein determining said ratio comprises accessing the value of said capacitance of the biosensor when completely filled with said sample from the memory storage means of a microprocessor.

22. A system for determining the volume of a biological sample within an electrochemical cell having a surface area and a volume, comprising:
   a voltage supply configured for applying a voltage to said electrochemical cell;
   means for measuring a current generated by said cell when said voltage is applied to said cell;
   means for deriving the capacitance of said cell from said measured current;
   means for deriving the surface area of said cell covered by said biological sample from said cell capacitance; and
   means for deriving the volume of said biological sample from said cell surface area.

23. The system of claim 22 further comprising means for determining whether said sample volume is adequate for making an accurate measurement of the concentration of one or more selected analytes within said biological sample.

24. The system of claim 23 further comprising:
   means for measuring the concentration of one or more selected analytes within said biological sample; and
   means for compensating for said sample volume determined to be inadequate while measuring the concentration of one or more selected analytes within said biological sample.

25. The system of claim 24 further comprising means for displaying the measured concentration of one or more selected analytes within said biological sample.

26. A kit for determining the volume of a biological sample within an electrochemical cell, comprising:
   a system according to claim 22; and
   an automated device integral with said system configured to operatively receive and engage said electrochemical cell for determining one or more physical or chemical characteristics of the biological sample.

27. A system for use with a meter configured for engaging an electrochemical cell and measuring the concentration of one or more selected analytes within a biological sample held within the electrochemical cell, said system comprising:
   a voltage supply configured for applying an alternating and/or a direct current voltage to said cell; and
   an electronic circuit configured for receiving a current generated by said electrochemical cell when a voltage is applied to said cell, measuring said generated current, determining the capacitance of said cell from said measured current, determining the surface area of said cell covered by said biological sample from said cell capacitance, and determining the volume of said biological sample from said cell surface area covered by said biological sample.

28. The system of claim 27 wherein said electronic circuit is further configured for determining whether said sample volume is adequate for making an accurate measurement of one or more selected physical or chemical characteristics of said biological sample.

29. The system of claim 28 wherein said electronic circuit is further configured for compensating for said sample volume if it is determined to be inadequate while measuring one or more selected physical or chemical characteristics of said biological sample.

30. The system of claim 29 wherein said electronic circuit is further configured for displaying said one or more measured characteristics of said biological sample.

31. The system of claim 27 wherein said electronic circuit comprises a microprocessor.

32. A system for measuring selected characteristics of a biological sample held within a test strip, comprising;
   a meter configured to receive said test strip and comprising a voltage supply configured for applying an alternating and/or a direct voltage to said test strip; and
   a microprocessor electronically coupled to said meter and comprising:
      (i) means for storing data related to said test strip, said biological sample, calibration and performance parameters of said meter;
      (ii) means for receiving a current generated by said electrochemical test strip when a voltage is applied to said test strip;
      (iii) means for measuring said generated current; and
      (iv) means for determining the volume of said biological sample from said test strip surface area covered by said biological sample based on said measured current.

33. The system of claim 32 wherein said microprocessor further comprises means for determining the adequacy of said sample volume for measuring said selected characteristics and means for compensating a selected characteristic measurement for an inadequate sample volume.

34. An electronic circuit configured for operatively receiving and engaging an electrochemical cell configured to hold a biological sample, said circuit comprising:
   means for measuring a current generated by said cell;
   means for deriving the capacitance and resistance of said cell from said measured current;
   means for deriving the surface area of said cell covered by said biological sample from said cell capacitance or from the ratio of said cell capacitance to said cell resistance; and
   means for deriving the volume of said biological sample from said cell surface area.

* * * * *